United States Patent [19]

Sakakibara

[11] 4,215,047
[45] Jul. 29, 1980

[54] 7-(ARGINYLAMINO)-4-METHYLCOUMARINS

[75] Inventor: Shumpei Sakakibara, Suita, Japan

[73] Assignee: Ajinomoto Company Incorporated, Tokyo, Japan

[21] Appl. No.: 912,851

[22] Filed: Jun. 5, 1978

[30] Foreign Application Priority Data

Jun. 6, 1977 [JP] Japan .................................. 52-66517
Jun. 8, 1977 [JP] Japan .................................. 52-67718
Jun. 8, 1977 [JP] Japan .................................. 52-67719

[51] Int. Cl.² .................. C07D 405/12; C07D 311/20
[52] U.S. Cl. .......................... 260/326.34; 260/326.25; 260/343.45
[58] Field of Search ...................... 260/326.34, 326.25, 260/343.45

[56] References Cited

U.S. PATENT DOCUMENTS 2,929,822  3/1960  Haisermann ................... 260/343.45

FOREIGN PATENT DOCUMENTS 1293160  4/1969  Fed. Rep. of Germany ...... 260/326.43

Primary Examiner—Mary C. Lee
Attorney, Agent, or Firm—Oblon, Fisher, Spivak, McClelland & Maier

[57] ABSTRACT

Peptide derivatives useful as fluorogenic substrates for determining enzymatic activities have the following formula

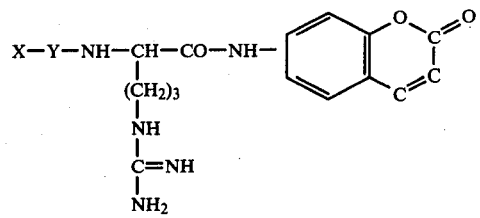

wherein Y is H or

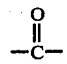

and X is a radical selected from the group consisting of

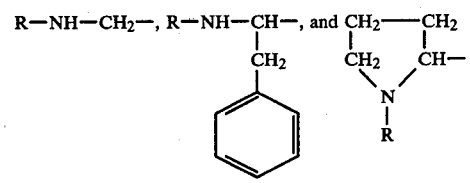

wherein R is a radical selected from the group consisting of hydrogen, amino-protecting groups, amino acid residues, terminal amino-protected amino acid residues, oligopeptide residues and terminal amino-protected oligopeptide residues.

25 Claims, No Drawings

7-(ARGINYLAMINO)-4-METHYLCOUMARINS

This invention relates to peptide derivatives, more particularly 7-($N^\alpha$-substituted or non-substituted-X-arginyl)-amino-4-methylcoumarins wherein X is a residue of an amino acid selected from the group consisting of glycine, phenylalanine and proline, and acid addition salts thereof, which are useful as fluorogenic substrates for determining enzymatic activities.

In order to determine enzymatic activities, a method is usually employed which comprises reacting material which is specifically acted on by an enzyme with the enzyme and comparing the state of the material before reaction with that after reaction.

Natural material can be used in this determination, but synthesized ones are suitably employed in view of mass production and production in pure form. Therefore, compounds which can be substrates for all sorts of enzymes are greatly desired. Such compounds can be antimetabolites in vivo, and thus it is expected that such compounds can be used as medicines.

This invention responds to such desires and provides synthetic substrates which show specificity to enzymes such as Trypsin and Thrombin.

Compounds of the present invention are novel peptide derivatives, which are not described in any publications, more particularly 7-($N^\alpha$-substituted or non-substituted-X-arginyl)amino-4-methyl coumarins wherein X is a residue of an amino acid selected from the group consisting of glycine, phenylalanine and proline, and acid addition salts thereof.

(1) When X is a residue of glycine, the compounds have the following formula:

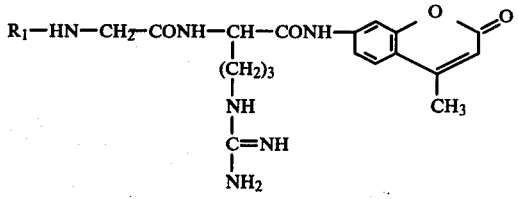

and salts thereof wherein $R_1$ is a radical selected from the group consisting of hydrogen, amino-protecting groups, and $N^\alpha$-substituted or non-substituted prolyl, glutamyl, seryl and leucyl groups.

When $R_1$ is hydrogen, the compound is 7-(glycylarginyl)amino-4-methylcoumarin. When $R_1$ is a prolyl group, the compound is 7-(prolylglycylarginyl)amino-4-methylcoumarin. When $R_1$ is a glutamyl group, the compound is 7-(glutamylglycylarginyl)amino-4-methylcoumarin. When $R_1$ is a seryl group, the compound is 7-(serylglycylarginyl)amino-4-methylcoumarin. When $R_1$ is a leucyl group, the compound is 7-(leucylglycylarginyl)amino-4-methylcoumarin. When $R_1$ is a glutamyl group having an isoleucyl group in the $N^\alpha$-position thereof, namely an isoleucylglutamyl group, the compound is 7-(isoleucylglutamylglycylarginyl)amino-4-methylcoumarin. When $R_1$ is a seryl group having a valyl group in the $N^\alpha$-position thereof, namely a valylseryl group, the compound is 7-(valylserylglycylarginyl)amino-4-methylcoumarin. When $R_1$ is a leucyl group having a valyl group in the $N^\alpha$-position thereof, namely a valylleucyl group, the compound is 7-(valylleucylglycylarginyl)amino-4-methylcoumarin.

(2) When X is a residue of phenylalanine, the compounds of the present invention have the following formula:

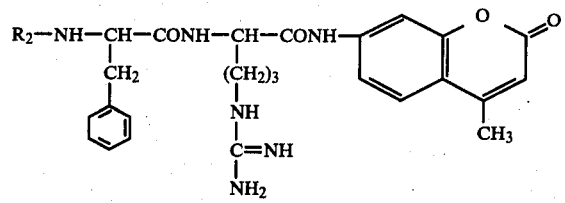

and salts thereof wherein $R_2$ is a radical selected from the group consisting of hydrogen, amino-protecting groups and a prolyl group whose imino group is protected or not protected. When $R_2$ is hydrogen, the compound is 7-(phenylalanylarginyl)amino-4-methylcoumarin. When $R_2$ is a prolyl group, the compound is 7-(prolylphenylalanylarginyl)amino-4-methylcoumarin.

(3) When X is the residue of proline, the compounds of the present invention have the following formula:

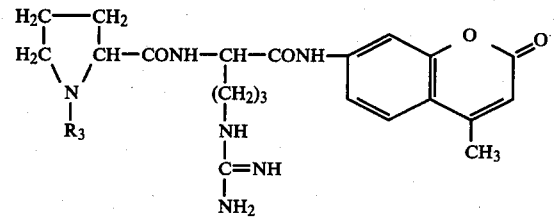

and salts thereof wherein $R_3$ is a radical selected from the group consisting of hydrogen, imino-protecting groups and a valyl group whose amino group is protected or not protected.

When $R_3$ is hydrogen, the compound is 7-(prolylarginyl)amino-4-methylcoumarin. When $R_3$ is a valyl group, the compound is 7-(valylprolylarginyl)amino-4-methylcoumarin.

$N^\alpha$-amino and imino groups in such compounds may be protected by conventional protecting groups for peptides, such as acyl groups (for example, the acetyl group and the benzoyl group), the carbobenzoxy group, the tert-alkyloxycarbonyl group, the tosyl group and the glutary group.

In compounds having a serine residue, the hydroxy group thereof may be protected by a protecting group which is used in the conventional methods for synthesizing peptides, such as an alkyl group and the benzyl group.

In compounds having a glutamic acid residue, the γ-carboxyl group thereof may be protected by an ester group formed with an alcohol such as benzyl alcohol.

The guanidino group of arginine which is formed in these compounds may be protected by N-guanidino-protecting groups which are used in the conventional method for synthesizing peptides, such as the nitro group, the tosyl group and the p-methoxybenzenesulfonyl group, and by adding a proton such as by reacting it with an acid.

The compounds of the present invention can be produced by conventional methods for synthesizing peptides using 7-arginylamino-4-methylcoumarin. For example, 7-(glycylarginyl)amino-4-methylcoumarin can be produced by reacting glycine whose amino group has been protected, with 7-arginylamino-4-methylcoumarin in the presence of a condensing agent such as dicyclohexylcarbodiimide (DCCI), or reacting an active ester of glycine whose amino group has been protected, with 7-arginylamino-4-methylcoumarin, and then removing the protecting group. By reacting this compound with glutamic acid whose amino group and γ-carboxyl group are protected and then removing the protecting groups from both the amino group and the γ-carboxyl group of the thus obtained compound, 7-(glutamylglycylarginyl)amino-4-methylcoumarin can be obtained. 7-(Isoleucylglutamylglycylarginyl)amino-4-methylcoumarin can be produced by reacting 7-(glutamylglycylarginyl)amino-4-methylcoumarin as produced above, with an active ester of isoleucine whose amino group has been protected, and then treating the thus reacted material in the same manner as above. 7(Prolylglycyl)arginyl)amino-4-methylcoumarin can be produced by reacting 7-(glycylarginyl)amino-4-methylcoumarin obtained above with proline whose imino group has been protected and then removing the protecting group from the thus obtained compound.

These condensing reactions can be conveniently carried out in a suitable solvent such as dimethylformamide (DMF), dimethylsulfoxide, water and the mixtures thereof.

It is preferable that the carboxyl group which reacts with the amino group, be in the active ester form. Suitable examples of active esters are the N-hydroxysuccinimide ester and the p-nitrophenyl ester. Reactions using an active ester can be carried out satisfactorily at room temperature, but can be accelerated by heating, if necessary.

After completing the reaction, the reaction mixture is concentrated to yield solid material and the material is purified by column chromatography and then lyophilized. Compounds thus obtained are usually white powders decomposed slowly by heating above 140° C.

As regards the compounds having a protecting group on the amino or imino group, such a protecting-group can be removed by conventional methods used in synthesizing peptides. For example, a carbobenzoxy group can be removed by catalytic hydrogenation in a solvent such as alcohol, and a tert-butyloxycarbonyl group can be removed by reacting the compound in hydrogen fluoride for 30 minutes or by reacting the compound with p-toluenesulfonic acid for 90 minutes.

The compounds of the present invention can be produced in the free base form or as acid addition salts according to the method of preparation. A free base form can be easily converted to the salt thereof and an acid addition salt can be easily converted to the free base form thereof.

Examples of the acid addition salts are salts with inorganic acids such as hydrochloric acid, sulfuric acid, nitric acid and phosphoric acid, and salts with organic acids such as acetic acid, oxalic acid, tartaric acid, succinic acid, citric acid and toluene sulfonic acid.

Chemical structures of the compounds in the present invention were identified by elemental analysis, amino acid analysis, ultraviolet spectrum, and comparison of the ultraviolet spectrum of material hydrolyzed with trypsin with 7-amino-4-methylcoumarin.

The compounds of the present invention are all hydrolyzed specifically by one or more enzyme(s) such as Thrombin, Horseshoe-Crab Blood Coagulating Enzyme, urokinase and/or Blood Coagulating Factor XII$_a$, and therefore are suitable for synthetic substrates of these compounds.

The amino acids which compose the compounds of the present invention may have any stereochemical configuration, L, D and DL, if the compounds can be enzymatically hydrolyzed.

Now, 7-arginylamino-4-methylcoumarin and the salts thereof are also new compounds. 7-Arginylamino-4-methylcoumarin in the free base form can be easily produced by reacting the acid salts thereof with an alkaline material.

The present invention is illustrated in more detail by the following Examples.

EXAMPLE 1

N$^\alpha$-carbobenzoxy-L-arginine hydrochloric acid salt (69.0 g, 0.2 M) and 7-amino-4-methylcoumarin (17.5 g, 0.1 M) were dissolved in dimethylformamide (DMF) (300 ml). Dicyclohexylcarbodiimide (DCCD) (21 g, 0.1 M) was added to the mixture with stirring at room temperature. This mixture was stirred overnight at room temperature, and the produced dicyclohexyl urea was removed by filtration. The obtained filtrate was concentrated under reduced pressure and to the thus obtained residue methyl alcohol (50 ml) and ethyl acetate (500 ml) were added. The precipitated material was separated by filtration to give crude crystals (19 g). These crystals were dissolved in a mixture of heated DMF (30 ml) and heated methyl alcohol (100 ml) and insoluble material was removed by filtration. To the filtrate ethyl acetate (400 ml) was added and the thereby precipitated white crystals were separated by filtration and dried to give 7-(N$^\alpha$-carbobenzoxy-L-arginyl)amino-4-methylcoumarin hydrochloric acid salt (14.5 g, yield: 29%).

m.p. 210°-211° C. (dec.).

$[\alpha]_D^{15}$ −17.0° (C=2.35, DMF)

| Elemental Analysis: | C | H | N% |
|---|---|---|---|
| Calcd. for C$_{24}$H$_{28}$N$_5$O$_5$Cl: | 57.42 | 5.62 | 13.96 |
| Found: | 57.61 | 5.69 | 13.94 |

7-(N$^\alpha$-carbobenzoxy-L-arginyl)amino-4-methylcoumarin hydrochloric acid salt (251 mg, 0.5 mM) was dissolved in a mixture of methyl alcohol (50 ml), acetic acid (5 ml) and water (10 ml), and 5% palladium-carbon catalyst (25 mg) was added thereto. This mixture was stirred while being treated with hydrogen gas at room temperature. The catalyst was removed by filtration, and from the filtrate the solvent was distilled off under reduced pressure. To the residue ether (50 ml) was added and the precipitated powder was separated by filtration to give 7-L-arginylamino-4-methylcoumarin hydrochloric acid salt hemihydrate (188 mg, yield: 100%).

m.p. 275° C. (dec.)

$[\alpha]_D^{15}$ +19.9° (C=1.01, 25% CH$_3$COOH)

This product gave a single spot on the thin layer chromatogram (silica gel) with a ternary eluent of n-butyl alcohol, acetic acid and water in 4:1:1 volume ratio.

| Elemental Analysis: | C | H | N% |
|---|---|---|---|
| Calcd. for C$_{16}$H$_{22}$N$_5$O$_3$Cl ½H$_2$O: | 50.99 | 6.15 | 18.59 |
| Found: | 51.02 | 6.11 | 18.41 |

7-L-arginylamino-4-methylcoumarin hydrochloric acid salt hemihydrate (1.51 g, 4 mM) was dissolved in a mixture of DMF (10 ml) and water (10 ml) and the N-hydroxysuccinimide ester of carbobenzoxyglycine (1.53 g, 5 mM) was added thereto. The mixture was stirred for 15 hours and then concentrated to yield solid material. This material was purified by column chromatography (2×20 cm) using silica gel as adsorbent and a ternary eluent of chloroform, methyl alcohol and acetic acid in 95:5:3 volume ratio. The main fraction was concentrated to yield solid material and this material was dissolved in acetic acid (50 ml). This solution was lyophilized to give 7-($N^\alpha$-carbobenzoxyglycyl-L-arginyl-)amino-4-methylcoumarin hydrochloric acid salt [I] (1.67 g).

m.p. 150° C. (dec.)

$[\alpha]_D^{15}$ −37.6° (C=0.56, DMF)

| Elemental Analysis: | C | H | N% |
|---|---|---|---|
| Calcd. for $C_{26}H_{31}N_6O_6Cl \cdot H_2O \cdot CH_3COOH$: | 52.78 | 5.70 | 13.19 |
| Found: | 52.72 | 5.49 | 13.48 |

EXAMPLE 2

7-($N^\alpha$-carbobenzoxyglycyl-L-arginyl)amino-4-methylcoumarin hydrochloric acid salt (559 mg, 1 mM) was dissolved in methyl alcohol (50 ml) and palladium-carbon catalyst (50 mg) was added thereto. This mixture was stirred while being treated with hydrogen gas for 3 hours. The catalyst was removed by filtration and the thus obtained filtrate was concentrated to yield solid material. To the residue ether (50 ml) was added to yield a powder. The powder was separated by filtration and dried to give 7-(glycyl-L-arginyl)amino-4-methylcoumarin hydrochloric acid salt [II] (400 mg).

m.p. 145° C. (dec.)

$[\alpha]_D^{15}$ −28.5° (C=0.43, DMF)

| Elemental Analysis: | C | H | N% |
|---|---|---|---|
| Calcd. for $C_{18}H_{25}N_6O_4Cl \cdot H_2O \cdot 2CH_3COOH$: | 46.92 | 6.27 | 14.93 |
| Found: | 47.15 | 6.42 | 14.53 |

EXAMPLE 3

7-($N^\alpha$-glycyl-L-arginyl)amino-4-methylcoumarin hydrochloric acid salt (425 mg, 1 mM) was dissolved in DMF (10 ml), and the N-hydroxysuccinimide ester of carbobenzoxy-L-proline (450 mg, 1.3 mM) was added thereto. The mixture was stirred for 15 hours at room temperature and then was concentrated to yield solid material. This material was purified by column chromatography (2×10 cm) using silica gel as adsorbent and a ternary eluent of chloroform, methyl alcohol and acetic acid in 95:5:3 volume ratio. The main fraction was concentrated to yield solid material. This material was dissolved in acetic acid (20 ml) and lyophilized to give 7-($N^\alpha$-carbobenzoxy-L-prolylglycyl-L-arginyl)amino-4-methylcoumarin hydrochloric acid salt as the acetic acid adduct [III] (460 mg).

m.p. 200° C. (dec.)

$[\alpha]_D^{15}$ −47.6° (c=0.66, DMF)

| Elemental Analysis: | C | H | N% |
|---|---|---|---|
| Calcd. for $C_{31}H_{38}N_7O_7Cl \cdot H_2O \cdot CH_3COOH$: | 53.98 | 6.04 | 13.36 |
| Found: | 53.42 | 5.61 | 13.53 |

EXAMPLE 4

7-($N^\alpha$-carbobenzoxy-L-prolylglycyl-L-arginyl-)amino-4-methylcoumarin hydrochloric acid salt (200 mg, 0.27 mM) was dissolved in methyl alcohol (50 ml) and 1 N HCl (0.27 ml) and palladium-carbon catalyst (20 mg) were added thereto. This mixture was stirred while being treated with hydrogen gas for 3 hours. The catalyst was removed by filtration and the filtrate was concentrated to yield solid material. To the residue ether (50 ml) was added and the thus produced powder was separated by filtration to give 7-(L-prolylglycyl-L-arginyl)amino-4-methylcoumarin hydrochloric acid salt [IV] (150 mg).

m.p. 185° C. (dec.)

$[\alpha]_D^{15}$ −47.7° (C=1.73, 80% DMF)

| Elemental Analysis: | C | H | N% |
|---|---|---|---|
| Calcd. for $C_{23}H_{33}N_7O_5Cl_2 \cdot CH_3COOH \cdot 3H_2O$: | 44.64 | 6.44 | 14.58 |
| Found: | 44.93 | 5.97 | 14.72 |

EXAMPLE 5

$N^\alpha$-carbobenzoxy-$N^G$-tosyl-L-arginyl (See J. A.C.S. 82, 4576) (6.0 g, 13 mM) was dissolved in DMF (20 ml), and 4-methyl-7-aminocoumarin (1.75 g, 10 mM) was added thereto. To this mixture DCCD (2.47 g, 12 mM) was added with ice-cooling. The mixture was stirred overnight at room temperature and then precipitated dicyclohexyl urea was removed by filtration. DMF was distilled off under reduced pressure, and to the residue chloroform (200 ml) was added for extraction. The chloroform solution was washed with 1 N CHl, 5% NaHCO₃ and water successively, and then was dried over anhydrous sodium sulfate. Next, chloroform was distilled off under reduced pressure, and the residue was purified by column chromatography using silica gel and a binary mixture of chloroform and ethyl acetate in 2:1 volume ratio. Main fractions were combined and concentrated. The residue was dissolved in chloroform (10 ml) and ether was added thereto to precipitate the desired material. This material was separated to give 7-(Nα-carbobenzoxy-NG-tosyl-L-arginyl)amino-4-methylcourmarin (2.31 g, yield: 37%).

m.p. 155.0–162.5° C. (dec.)

$[\alpha]_D^{18}$ +11.2° (C=0.5, DMF)

This product gave a single spot (Rf=0.4) on the thin layer chromatogram (silica gel) with a ternary eluent of chloroform, methyl alcohol and acetic acid in 95:5:3 volume ratio.

| Elemental Analysis: | C | H | N% |
|---|---|---|---|
| Calcd. for $C_{31}H_{33}N_5O_7S \cdot \frac{1}{2} H_2O$: | 59.22 | 5.45 | 11.14 |
| Found: | 59.15 | 5.29 | 11.27 |

7-($N^\alpha$-carbobenzoxy-$N^G$-tosyl-L-arginyl)amino-4-methycoumarin (500 mg) was dissolved in methyl alcohol (50 ml), and 5% palladium-carbon catalyst (50 mg) was added thereto. The mixture was treated with hydrogen gas for 5 hours with stirring. From the reaction mixture, the catalyst was removed by filtration and from the filtrate methyl alcohol was distilled off under reduced pressure The residue was dissolved in methanol (5 ml) and ether was added to yield a precipitate. The precipitate was separated and dried to give 7-(N$^G$-tosyl-L-arginyl)amino-4-methylcoumarin (340 mg, yield: 87.1%).

m.p. 174.5°–182.5° C. (dec.)

$[\alpha]_D^{18}$ −11.4° (C=0.5, DMF)

This product gave a single spot (Rf=0.6) on the thin layer chromatogram (silica gel) with a ternary eluent of n-butyl alcohol, acetic acid and water in 4:1:1 volume ratio.

| Elemental Analysis: | C | H | N % |
|---|---|---|---|
| Calcd. for C$_{23}$H$_{27}$N$_5$O$_5$S . ½H$_2$O: | 54.86 | 5.80 | 13.91 |
| Found: | 54.41 | 5.72 | 13.60 |

7-(N$^G$-tosyl-L-arginyl)amino-4-methylcoumarin (490 mg, 1 mM) was dissolved in DMF (5 ml), and the N-hydroxysuccinimide ester of carbobenzoxyglycine (459 mg, 1.5 mM) was added thereto. This mixture was stirred for 2 days at room temperature. To this mixture, excess ether was added to yield a precipitate. This precipitate was separated by filtration, dried, and purified by column chromatography (2×10 cm) using silica gel as adsorbent and a ternary eluent of chloroform, ethyl acetate and ethyl alcohol in 5:5:2 volume ratio. The main fractions were combined and concentrated to yield solid material. The residue was recrystalized from a binary mixture of methyl alcohol (5 ml) and ether (30 ml) to give 7-(N$^\alpha$-carbobenzoxyglycyl-L-N$^G$-tosylarginyl)amino-4-methylcoumarin (611 mg, yield: 90.1%).

m.p. 130.5°–135.5° C.

$[\alpha]_D^{15}$ −30.1° (C=1, DMF)

| Elemental Analysis: | C | H | N % |
|---|---|---|---|
| Calcd. for C$_{33}$H$_{36}$N$_6$O$_8$S . ½ H$_2$O: | 57.80 | 5.44 | 12.26 |
| Found: | 57.69 | 5.30 | 12.10 |

EXAMPLE 6

7-(N$^\alpha$-carbobenzoxyglycyl-N$^G$-tosyl-arginyl)amino-4-methylcoumarin (678 mg, 1 mM) was dissolved in a mixture of methyl alcohol (50 ml) and acetic acid (10 ml), and 5% palladium-carbon catalyst (50 mg) was added thereto. This mixture was treated with hydrogen gas for 4 hours. The catalyst was removed by filtration and from the filtrate, solvent was distilled off under reduced pressure. The residue was dissolved in methyl alcohol (10 ml) and excess ether was added thereto to yield a precipitate.

The precipitate was separated by filtration and dried. The precipitate was dissolved in DMF (8 ml), and the N-hydroxysuccinimide ester of tert-butyloxycarbonyl-γ-benzyl-L-glutamic acid (478 mg, 1.1 mM) was added. This mixture was stirred for 2 days at room temperature, and excess ether was added to yield a precipitate. This precipitate was separated by filtration and purified by column chromatography (2×10 cm) using silica gel as adsorbent and a ternary eluent of chloroform, ethyl acetate and ethyl alcohol in 5:5:2 volume ratio. The main fractions were combined and concentrated to yield a solid material. This material was reprecipitated from a binary mixture of methyl alcohol (10 ml) and ether (50 ml) to give 7-(N$^\alpha$-tert-butyloxycarbonyl-γ-benzyl-L-glutamylglycyl-N$^G$-tosyl-L-arginyl)amino-4-methylcoumarin (705 mg, yield 82.0%).

m.p. 118.5°–123.5° C.

$[\alpha]_D^{15}$ −12.7° (C=1, DMF)

| Elemental Analysis: | C | H | N % |
|---|---|---|---|
| Calcd. for C$_{42}$H$_{51}$N$_7$O$_{11}$S½H$_2$O: | 57.92 | 6.02 | 11.26 |
| Found: | 57.85 | 6.30 | 11.42 |

EXAMPLE 7

To a mixture of 7-(N$^\alpha$-tert-butyloxycarbonyl-γ-benzyl-L-glutamylglycyl-N$^G$-tosyl-L-arginyl)amino-4-methylcoumarin (432 mg, 0.5 mM) and anisole (0.5 ml), anhydrous hydrogen fluoride (10 ml) was added at −70° C. This mixture was stirred for 60 minutes with cooling in ice bath. The excess hydrogen fluoride was distilled out under reduced pressure. To this residue water (5 ml) was added and the thus obtained water layer was washed with ether (20 ml) and then passed through a column containing an ion-exchange resin, Dowex 1×2 (acetic acid salt form, 5 ml), which was eluted with water (10 ml). The eluate was lyophilized to give 7-(L-glutamylglycyl-L-arginyl)amino-4-methylcoumarin [V] (225 mg, yield: 74%), which is amorphous.

$[\alpha]_D^{15}$ +29.5° (C=0.5, DMF)

| Elemental Analysis: | C | H | N % |
|---|---|---|---|
| Calcd. for C$_{23}$H$_{31}$O$_7$N$_7$ . CH$_3$COOH . 2H$_2$O: | 48.93 | 6.41 | 15.98 |
| Found: | 48.75 | 6.20 | 16.11 |

EXAMPLE 8

7-(L-glutamylglycyl-L-arginyl)amino-4-methylcoumarin (100 mg, 0.18 mM) was dissolved in DMF (2 ml), and triethylamine (0.03 ml) was added thereto with stirring and cooling. This mixture was adjusted to pH about 7, and then p-nitrophenyl acetate (36.1 mg, 0.23 mM) was added thereto. This mixture was stirred for 2 days at room temperature. Excess ether was added to the mixture and the produced precipitate was separated by filtration and dried. This product was dissolved in 80% methyl alcohol (2 ml) and ethyl acetate (30 ml) was added thereto for re-precipitation to give 7-(N$^\alpha$-acetyl-L-glutamylglycyl-L-arginyl)amino-4-methylcoumarin [VI] (99 mg, yield: 84.9%).

m.p. 214.0°–217.5° C. (dec.)

$[\alpha]_D^{20}$ −13.8° (C=1, DMF)

| Elemental Analysis: | C | H | N % |
|---|---|---|---|
| Calcd. for C$_{25}$H$_{33}$O$_8$N$_7$ . CH$_3$COOH . ½H$_2$O: | 51.58 | 6.09 | 15.60 |
| Found: | 51.21 | 6.18 | 16.12 |

EXAMPLE 9

7-(L-glutamylglycyl-L-arginyl)amino-4-methylcoumarin (100 mg, 0.18 mM) was dissolved in DMF (2 ml), and triethylamine (0.03 ml) was added thereto with stirring and cooling. This mixture was adjusted to pH about 7, and the N-hydroxysuccinimide ester of tert-butyloxycarbonyl-L-isoleucine (75.4 mg, 0.23 mM) was added thereto. This mixture was stirred for 3 days at room temperature. To this mixture excess ether was added and the produced precipitate was separated by filtration and dried. This material was dissolved in methyl alcohol (2 ml), and ether (20 ml) was added thereto for reprecipitation to give 7-(N$^\alpha$-tert-butyloxycarbonyl-L-isoleucyl-L-glutamylglycyl-L-arginyl-)amino-4-methylcoumarin [VII] (120 mg, yield: 86.3%).
m.p. 208.0°—212.0° C. (dec.)
$[\alpha]_D^{20}$ −16.7° (C=1, DMF)

| Elemental Analysis: | C | H | N % |
|---|---|---|---|
| Calcd. for $C_{34}H_{50}O_{10}N_8 \cdot 2H_2O$: | 53.25 | 7.10 | 14.61 |
| Found: | 53.57 | 6.88 | 14.40 |

EXAMPLE 10

7-(N$^\alpha$-glycyl-L-arginyl)amino-4-methyl-coumarin hydrochloric acid salt (255 mg, 0.6 mM) was dissolved in a mixture of DMF (1 ml) and water (1 ml), and glutaric acid anhydride (75.2 mg, 0.66 mM) was added thereto. This mixture was stirred for 15 hours at room temperature, and ether (50 ml) was added to yield a precipitate. The precipitate was separated by filtration, dried and purified by column chromatography (2×15 cm) using silica gel as adsorbent and a binary eluent of chloroform and methyl alcohol in 1:2 volume ratio. The main fraction was concentrated to yield a solid material. This material was re-recipitated from DMF (5 ml)-ether (5 ml) to give 7-(N$^\alpha$-glutarylglycyl-L-arginyl)amino-4-methylcoumarin hydrochloric acid salt [VIII] (250 mg, yield: 77.4%).
m.p. 234.5°; 238.0° C. (dec.)
$[\alpha]_D^{15}$ +23.3° (C=1, DMF)

| Elemental Analysis: | C | H | N % |
|---|---|---|---|
| Calcd. for $C_{23}H_{31}O_7N_6Cl \cdot \frac{1}{4} H_2O$: | 50.82 | 5.84 | 15.46 |
| Found: | 51.25 | 5.80 | 15.60 |

EXAMPLE 11

7-L-arginylamino-4-methylcoumarin hydrochloric acid salt hemihydrate (377 mg, 1 mM) was dissolved in a mixture of DMF (10 ml) and water (10 ml), and N$^\alpha$-tert-butyloxycarbonyl-L-valyl-L-seryl-glycine-N-hydroxysuccinimide ester (458 mg, 1 mM) was added thereto. This mixture was stirred for 15 hours at room temperature and concentrated to yield a solid material. The residue was purified by column chromatography (2×15 cm) using silica gel as adsorbent and ternary mixtures of chloroform, methyl alcohol and acetic acid 95:5:3 (adsorption) and then 85:20:5 (elution) in volume ratios. The main fraction was concentrated to yield a solid material. The material was dissolved in acetic acid (50 ml) and lyophilized to give 7-(N$^\alpha$-tert-butyloxycarbonyl-L-valyl-L-seryl-glycyl-L-arginyl)amino-4-methylcoumrin hydrochloric acid salt [IX] (320 mg).
m.p. 160° C. (dec.)
$[\alpha]_D^{21}$ −21.1° (C=1.15, 80% DMF)

| Elemental Analysis: | C | H | N % |
|---|---|---|---|
| Calcd. for $C_{31}H_{47}O_9N_8Cl \cdot CH_3COOH \cdot 2H_2O$: | 49.09 | 6.87 | 13.88 |
| Found: | 48.65 | 6.82 | 14.07 |

EXAMPLE 12

7-(N$^\alpha$-tert-butyloxycarbonyl-O-benzyl-L-serylglycyl-L-arginyl)amino-4-methylcoumarin hydrochloric acid salt (120 mg, 0.28 mM) was dissolved in methyl alcohol (50 ml), and palladium-carbon catalyst (20 mg) was added. Through this mixture hydrogen gas was passed for 4 hours with stirring. The catalyst was removed by filtration and the filtrate was concentrted to yield a solid material. The residue was dissolved in acetic acid (10 ml) and lyophilized to give 7-(N$\alpha$-tert-butyloxycarbonyl-L-serylglycyl-L-arginyl)amino-4-methylcoumarin hydrochloric acid salt [X] (70 mg).
m.p. 180° C. (dec.)
$[\alpha]_D^{21}$ −28.4° (C=0.44, 80% DMF)

| Elemental Analysis: | C | H | N % |
|---|---|---|---|
| Calcd. for $C_{26}H_{38}N_7O_8Cl \cdot 3/2\ CH_3COOH$: | 49.60 | 6.32 | 13.97 |
| Found: | 50.11 | 6.47 | 13.65 |

EXAMPLE 13

7-(N$^\alpha$-glycyl-L-arginyl)amino-4-methyl-coumarin hydrochloric acid salt (230 mg, 0.54 mM) was dissolved in DMF (5 ml), and N$^\alpha$-tert-butyloxycarbonyl-O-benzyl-L-serine-N-hydroxysuccinimide ester (253 mg, 0.65 mM) was added thereto. This mixture was stirred for 15 hours at room temperature and concentrated to yield a solid material. The material was purified by column chromatography (2×15 cm) using silica gel as adsorbent and ternary mixtures of chloroform, methyl alcohol and acetic acid in 95:5:3 (adsorption) and then 85:20:5 (elution) volume ratio. The main fraction was concentrated to yield a solid material and dissolved in acetic acid (20 ml). This solution was lyophilized to give 7-(N$^\alpha$-tert-butyloxycarbonyl-O-benzyl-L-serylglycyl-L-arginyl)amino-4-methylcoumarin hydrochloric acid salt [XI] (180 mg).
m.p. 160° C. (dec.)
$[\alpha]_D^{21}$ −29.6° (C=0.46, 80% DMF)

| Elemental Analysis: | C | H | N% |
|---|---|---|---|
| Calcd. for $C_{33}H_{42}N_7O_8Cl \cdot CH_3COOH \cdot H_2O$: | 53.87 | 6.46 | 12.57 |
| Found: | 54.10 | 6.28 | 12.36 |

EXAMPLE 14

7-L-arginylamino-4-methylcoumarin hydrochloric acid salt hemihydrate (377 mg, 1 mM) was dissolved in a mixture of DMF (5 ml) and water (5 ml), N$^\alpha$-tert-butyloxycarbonyl-L-valyl-L-leucylglycine N-hydroxysuccinimide ester (484 mg, 1 mM) was added thereto. This mixture was stirred for 15 hours at room temperature and concentrated to yield a solid material. The material was purified by column chromatography (2×15 cm) using silica gel as adsorbent and ternary mixtures of chloroform, methyl alcohol and acetic acid in 95:5:3 (adsorption) and then 85:20:5 (elution) volume ratio. The main fraction was concentrated to yield a solid material, dissolved in acetic acid (20 ml) and lyophilized to give 7-(N$\alpha$-tert-butyloxycarbonyl-L-valyl-L-leucylglycyl-L-arginyl)amino-4-methylcoumarin hydrochloric acid salt [XII] (350 mg).
m.p. 150° C. (dec.)
$[\alpha]_D^{21}$ −35.9° (C=2.16, 80% DMF)

| Elemental Analysis: | C | H | N% |
|---|---|---|---|
| Calcd. for $C_{34}H_{53}N_8O_8Cl \cdot CH_3COOH \cdot 3H_2O$: | 50.78 | 7.46 | 13.16 |

-continued

| Elemental Analysis: | C | H | N% |
|---|---|---|---|
| Found: | 51.02 | 8.05 | 13.20 |

EXAMPLE 15

7-(N$^\alpha$-glycyl-L-arginyl)amino-4-methylcoumarin hydrochloric acid salt (91.4 mg, 0.215 mM) was dissolved in DMF (5 ml), and N-tert-butyloxycarbonyl-L-leucine N-hydroxysuccinimide ester (85 mg, 0.26 mM) was added thereto. This mixture was stirred for 15 hours at room temperature and concentrated to yield a solid material. The material was purified by column chromatography (1×15 cm) using silica gel as adsorbent and ternary mixtures of chloroform, methyl alcohol and acetic acid in 95:5:3 and then 85:20:5 volume ratio. The main fraction was concentrated to solid material, then dissolved in acetic acid (20 ml) and lyophilized to give 7-(N$^\alpha$-tert-butyloxycarbonyl-L-leucylglycyl-L-arginyl-)amino-4-methylcoumarin hydrochloric acid salt [XIII] (120 mg).
m.p. 160° C. (dec.)
$[\alpha]_D^{21}$ −37.8° (C=0.63, 80% DMF)

| Elemental Analysis: | C | H | N % |
|---|---|---|---|
| Calcd. for C$_{29}$H$_{44}$N$_7$O$_7$Cl.2CH$_3$COOH.H$_2$O: | 47.58 | 7.01 | 12.63 |
| Found: | 47.92 | 6.53 | 12.13 |

EXAMPLE 16

7-(N$^\alpha$-glycyl-L-arginyl)amino-4-methylcoumarin hydrochloric acid salt (136 mg, 0.32 mM) was dissolved in DMF (5 ml), and N$^\alpha$-carbobenzoxy-L-leucine N-hydroxysuccinimide ester (140 mg, 0.38 mM) was added thereto. This mixture was stirred for 15 hours at room temperature and concentrated to yield a solid material. The material was purified by column chromatography (1×15 cm) using silica gel and ternary mixtures of chloroform, methyl alcohol and acetic acid in 95:5:3 and then 85:20:5 volume ratio. The main fraction was concentrated to yield solid material, dissolved in acetic acid (20 ml) and lyophilized to give 7-(N$^\alpha$-carbobenzoxy-L-leucyclglycyl-L-arginyl)amino-4-methylcoumarin hydrochloric acid salt [XIV] (150 mg).
m.p. 150° C. (dec.)
$[\alpha]_D^{21}$ −35.1° (C=1.21, 80% DMF)

| Elemental Analysis: | C | H | N% |
|---|---|---|---|
| Calcd. for C$_{32}$H$_{42}$N$_7$O$_7$Cl CH$_3$COOH H$_2$O: | 54.43 | 6.45 | 13.07 |
| Found: | 54.35 | 5.95 | 12.83 |

EXAMPLE 17

7-L-arginylamino-4-methylcoumarin hydrochloric acid salt hemihydrate (754 mg, 2 mM) was dissolved in a mixture of DMF (10 ml) and water (10 ml), and carbobenzoxy-L-phenylalanine N-hydroxysuccinimide ester (1.03 g, 2.6 mM) was added thereto. This mixture was stirred for 15 hours at room temperature and concentrated to yield a solid material. The material was purified by column chromatography (2×15 cm) using silica gel as adsorbent and a ternary mixture of chloroform, methylalcohol and acetic acid in 95:5:3 volume ratio. The main fraction was concentrated to yield solid material, dissolved in acetic acid (30 ml) and lyophilized to give 7-(N$^\alpha$-carbobenzoxy-L-phenylalanyl-L-arginyl-)amino-4-methylcoumarin hydrochloric acid salt [XV] (920 mg).
m.p. 150° C. (dec.)
$[\alpha]_D^{15}$ −23.4° (C=0.65, DMF)

| Elemental Analysis: | C | H | N% |
|---|---|---|---|
| Calcd. for C$_{33}$H$_{37}$N$_6$O$_6$Cl: | 61.05 | 5.75 | 12.95 |
| Found: | 60.57 | 5.78 | 12.70 |

EXAMPLE 18

7-(N$^\alpha$-carbobenzoxy-L-phenylalanyl-L-arginyl-)amino-4-methylcoumarin hydrochloric acid salt (1.3 g, 2 mM) was dissolved in methyl alcohol (100 ml), and palladium-carbon catalyst (100 mg) was added. Through this mixture hydrogen gas was passed for 3 hours with stirring. The catalyst was removed by filtration and the filtrate was concentrated to yield a solid material. To the material ether (100 ml) was added and the thus produced powder was separated by filtration to give 7-(L-phenylalanyl-L-arginyl)-amino-4-methylcoumarin hydrochloric acid salt [XVI] (1.0 g).
m.p. 140° C. (dec.)
$[\alpha]_D^{15}$ −33.6° (C=0.52, DMF)

| Elemental Analysis: | C | H | N% |
|---|---|---|---|
| Calcd. for C$_{25}$H$_{31}$N$_6$O$_4$Cl . CH$_3$COOH . H$_2$O: | 54.67 | 6.29 | 14.17 |
| Found: | 54.86 | 6.68 | 14.09 |

EXAMPLE 19

7-(L-phenylalanyl-L-arginyl)amino-4-methylcoumarin hydrochloric acid salt (515 mg, 1 mM) was dissolved in DMF (5 ml), and carbobenzoxy-L-proline N-hydroxysuccinimide ester (450 mg, 1.3 mM) was added thereto. This mixture was stirred for 15 hours and concentrated to yield a solid material. The material was purified by column chromatography (2×15 cm) using silica gel as adsorbent and a ternary mixture of chloroform, methyl alcohol and acetic acid in 95:5:3 volume ratio. The main fraction was concentrated to yield a solid material. The solid material was dissolved in acetic acid and lyophilized to give 7-(N$^\alpha$-carbobenzoxy-L-prolyl-L-phenylalanyl-L-arginyl)amino-4-methylcoumarin hydrochloric acid salt as the acetic acid adduct [XVII] (510 mg).
m.p. 160° C. (dec.)
$[\alpha]_D^{15}$ −53.6° (C=0.75, DMF)

| Elemental Analysis: | C | H | N% |
|---|---|---|---|
| Calcd. for C$_{38}$H$_{44}$N$_7$O$_7$Cl . CH$_3$COOH: | 59.58 | 6.00 | 12.16 |
| Found: | 60.11 | 5.98 | 12.39 |

EXAMPLE 20

7-(N$^\alpha$-carbobenzoxy-L-prolyl-L-phenylalanyl-L-arginyl)amino-4-methylcoumarin hydrochloric acid salt (200 mg, 0.27 mM) was dissolved in methyl alcohol (50 ml), and 1 N HCl (0.27 ml) and palladium-carbon catalyst (20 mg) were added thereto. Through this mixture hydrogen gas was passed with stirring for 3 hours. The catalyst was removed by filtration and the filtrate was concentrated to yield a solid residue. To the residue ether (50 ml) was added and the thus produced powder was separated by filtration to give 7-(L-prolyl-L-phenylalanyl-L-arginyl)amino-4-methylcoumarin hydrochloric acid salt [XVIII] (150 mg).

m.p. 185° C. (dec.)
$[\alpha]_D^{21}$ −37.5° (C=1.52, 80% DMF)

| Elemental Analysis: | C | H | N % |
|---|---|---|---|
| Calcd. for $C_{30}H_{39}N_7O_5Cl_2 \cdot 4H_2O$: | 50.00 | 6.75 | 13.61 |
| Found: | 49.97 | 6.39 | 14.11 |

EXAMPLE 21

7-L-arginylamino-4-methylcoumarin hydrochloric acid salt hemihydrate (377 mg, 1 mM) was dissolved in a mixture of DMF (10 ml) and water (10 ml), and carbobenzoxy-L-proline N-hydroxysuccinimide ester (450 mg, 1.3 mM) was added thereto. This mixture was stirred for 15 hours at room temperature and concentrated to yield a solid material. The solid material was purified by column chromatography (2×15 cm) using silica gel as adsorbent and ternary mixtures of chloroform, methyl alcohol and acetic acid in 95:5:3 and then 85:20:5 volume ratio. The main fraction was concentrated to yield solid material, dissolved in acetic acid (10 ml), and lyophilized to give 7-($N^\alpha$-carbobenzoxy-L-prolyl-L-arginyl)amino-4-methylcoumarin hydrochloric acid salt [XIX] (530 mg).

m.p. 198° C. (dec.)
$[\alpha]_D^{15}$ −77.0° (C=0.6, DMF)

| Elemental Analysis: | C | H | N % |
|---|---|---|---|
| Calcd. for $C_{29}H_{35}N_6O_6Cl \cdot CH_3COOH$: | 56.48 | 5.96 | 12.75 |
| Found: | 56.21 | 5.74 | 13.07 |

The carbobenzoxy group of the compound thus obtained can be removed by a hydrogenation reaction in alcohol.

EXAMPLE 22

7-L-arginylamino-4-methylcoumarin hydrochloric acid salt hemihydrate (377 mg, 1 mM) was dissolved in a mixture of DMF (5 ml) and water (5 ml), and tert-butyloxycarbonyl-L-valyl-L-proline p-nitrophenyl ester (566 mg, 1.3 mM) was added thereto. The mixture was stirred for 15 hours at room temperature and concentrated to yield a solid material. The material was purified by column chromatography (2×15 cm) using silica gel as adsorbent and ternary mixtures of chloroform, methyl alcohol and acetic acid in 95:5:3 and then 85:20:5 volume ratio. The main fraction was concentrated to yield a solid material, dissolved in acetic acid (10 ml) and lyophilized to give 7-(Nα-tert-butyloxycarbonyl-L-valyl-L-propyl-L-arginyl)amino-4-methylcoumarin hydrochloric acid salt [XX] (320 mg).

m.p. 155° C. (dec.)
$[\alpha]_D^{15}$ −64.8° (C=0.66, DMF)

| Elemental Analysis: | C | H | N% |
|---|---|---|---|
| Calcd. for $C_{31}H_{46}N_7O_7Cl \cdot 2H_2O \cdot 2CH_3COOH$: | 51.24 | 7.13 | 11.95 |
| Found: | 51.38 | 6.81 | 11.86 |

Each compound produced above (0.1–0.2 mM) was dissolved in a mixture of dimethylsulfoxide (5 ml) and water (5 ml) and this solution was diluted with 0.05 M Tris-HCl buffer (pH 8.0) containing both 0.1 M NaCl and 10 mM $CaCl_2$ to adjust the total volume thereof to 500 ml and thereby a substrate solution was prepared.

Each substrate solution (2 ml) was added to a test tube and the thus prepared test tube was kept at 37° C. for 5 minutes. Then, each enzyme solution (20 μl) was added thereto and incubated at 37° C. for 20 minutes with stirring. Incubation was stopped by adding 100% acetic acid (0.5 ml) thereto.

The degree of hydrolysis was determined by measuring the fluorescence intensity at 460 nm with excitation at 380 nm in the fluorescence spectra. Results are listed in the following table.

Each value is the fluorescence intensity ratio to the fluorescence intensity of a 7-amino-4-methylcoumarin solution (40 μM, 40 μmole/l) considered as 100.

For value marked with an asterisk the fluorescence intensity of a 7-amino-4-methylcoumarin solution (200 μM, 200 μmol/l) is taken as 100.

In these experiments each enzyme was dissolved in the above buffer solution and used.

| Enzyme | Substrate (compound) | | | | | | | | | |
|---|---|---|---|---|---|---|---|---|---|---|
| | I | II | III | IV | V | VI | VII | VIII | IX | X |
| Thrombin produced by Mochida Pharmaceutical Co. (2Γ) | 10 | 6 | 33 | ** | ** | 10 | 16 | 12 | 26 | 66 |
| Purified Thrombin (2Γ) | ** | ** | ** | " | " | ** | ** | ** | 10 | 15 |
| Blood Coagulating Factor $X_a$ (1.6Γ) | " | " | " | " | 1 | 12 | 22 | 5 | 6 | 30 |
| Horseshoe-crab Blood Coagulating Enzyme (3Γ) | " | " | " | " | ** | 7 | 40* | 12 | 90 | 59* |
| Urokinase (10Γ) | 15 | 5 | " | 10 | 45* | 35 | 10 | 50* | 45* | 32 |
| Cattle Plasmin (1Γ) | ** | ** | " | ** | 3 | ** | 4 | 1 | 18 | 9 |
| Plasma Kallikrein (1Γ) | 1 | " | 1 | " | 1 | " | ** | ** | 9 | 11 |
| Pancreas Kallikrein (3.4Γ) | ** | " | ** | " | 6 | " | " | " | 4 | ** |
| Urine Kallikrein (2.5Γ) | " | " | " | " | 1 | " | " | " | 4 | " |
| Blood Coagulating Factor $IX_a$ (10Γ) | " | " | " | — | ** | " | " | " | ** | " |

-continued

| Blood Coagulating Factor XII$_a$ (0.0015 unit) | " | 1 | " | ** | " | " | " | " | 4 | " |

| Enzyme | Substrate (compound) | | | | | | | | | |
|---|---|---|---|---|---|---|---|---|---|---|
| | IX | XII | XIII | XIV | XV | XVI | XVII | XVIII | XIX | XX |
| Thrombin produced by Mochida Pharmaceutical Co. (2Γ) | 71 | 50 | 68 | 42* | 7 | ** | 10 | 7 | 80* | 80* |
| Purified Thrombin (2Γ) | 20 | 12 | 16 | 22 | ** | " | ** | ** | 40* | 82* |
| Blood Coagulating Factor X$_a$ (1.6Γ) | 36 | 21 | 27 | 29 | 1 | " | " | " | ** | 1 |
| Horseshoe-crab Blood Coagulating Enzyme (3Γ) | 71* | 54* | 62* | 62 | ** | " | " | " | " | 15 |
| Urokinase (10Γ) | 34 | 19 | 42 | 43 | " | " | " | " | " | ** |
| Cattle Plasmin (1Γ) | 19 | 17 | 9 | 21 | 42 | — | 42 | 43 | " | 40 |
| Plasma Kallikrein (1Γ) | 14 | 12 | 7 | 18 | 81 | " | 58 | 75 | 1 | ** |
| Pancreas Kallikrein (3.4Γ) | ** | ** | ** | 2 | 18 | 8 | 42* | 58* | ** | " |
| Urine Kallikrein (2.5Γ) | " | " | " | ** | 4 | ** | 4 | 30 | " | " |
| Blood Coagulating Factor IX$_a$ (10Γ) | " | " | " | " | ** | " | 1 | ** | 2-6 | 42-31 |
| Blood Coagulating Factor XII$_a$ (0.0015 unit) | " | " | " | " | " | " | ** | " | ** | ** |

**undetectable

What is claimed is:

1. A compound having the formula:

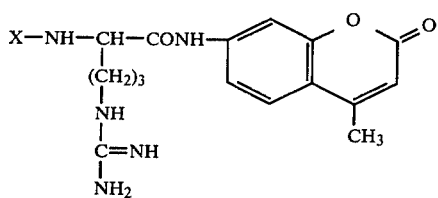

wherein X is a substituent selected from the group consisting of glycyl, prolylglycyl, glutamyl-glycyl, isoleucyl-glutamyl-glycyl, seryl-glycyl, valyl-seryl-glycyl, leucyl-glycyl, valyl-leucyl-glycyl, phenylalanyl, prolylphenylalanyl, prolyl, valyl-prolyl, and acid addition salts thereof.

2. The compound of claim 1, wherein at least one of the N$^2$-amino and imino groups in said compound is protected by an acetyl, benzoyl, carbobenzoxy, t-alkyloxycarbonyl, tosyl or glutaryl group.

3. The compound of claim 1, wherein the hydroxy substituent on the seryl substituent of said compound containing a seryl radical is protected with an alkyl or benzyl substituent.

4. The compound of claim 1, wherein the guanidino portion of the arginine residue in said compound is protected by a nitro, tosyl or p-methoxybenzene sulfonyl group or as a protonated salt.

5. The compound of claim 1, wherein the free carboxyl substituent on the glutamyl substituent of said compound containing a glutamyl substituent is protected as the benzyl ester.

6. The compound of claim 1 which is 7-(N$^\alpha$-carbobenzoxyglecyl-L-arginyl)amino-4-methylcoumarin.

7. The compound of claim 1 which is 7-(glycyl-L-arginyl)amino-4-methylcoumarin.

8. The compound of claim 1 which is 7-(N$^\alpha$-carbobenzoxy-L-prolylglycyl-L-arginyl)amino-4-methylcoumarin.

9. The compound of claim 1 which is 7-(L-prolylglycyl-L-arginyl)amino-4-methylcoumarin.

10. The compound of claim 1 which is 7-(L-glutamylglycyl-L-arginyl)amino-4-methylcoumarin.

11. The compound of claim 1 which is 7-N$^\alpha$-acetyl-L-glutamylglycyl-L-arginyl)amino-4-methylcoumarin.

12. The compound of claim 1 which is 7-(N$^\alpha$-tert-butoxycarbonyl-L-isoleucyl-L-glutamylglycyl-L-arginyl)amino-4-methylcoumarin.

13. The compound of claim 1 which is 7-(N$^\alpha$-glutarylglycyl-L-arginyl)amino-4-methylcoumarin.

14. The compound of claim 1 which is 7-(N$^\alpha$-tert-butoxycarbonyl-L-valyl-L-serylglycyl-L-arginyl)amino-4-methylcoumarin.

15. The compound of claim 1 which is 7-(N$^\alpha$-tert-butoxycarbonyl-L-serylglycyl-L-arginyl)amino-4-methylcoumarin.

16. The compound of claim 1 which is 7-N$^\alpha$-tert-butoxycarbonyl-O-benzyl-L-serylglycyl-L-arginyl)amino-4-methyl-coumarin.

17. The compound of claim 1 which is 7-(N$^\alpha$-tert-butoxycarbonyl-L-valyl-L-leucylglycyl-L-arginyl)amino-4-methyl-coumarin.

18. The compound of claim 1 which is 7-(N$^\alpha$-tert-butoxycarbonyl-L-leucylglycyl-L-arginyl)amino-4-methylcoumarin.

19. The compound of claim 1 which is 7-(N$^\alpha$-carbobenzoxy-L-leucylglycyl-L-arginyl)amino-4-methylcoumarin.

20. The compound of claim 1 which is 7-(N$^\alpha$-carbobenzoxy-L-phenylalanyl-L-arginyl)amino-4-methylcoumarin.

21. The compound of claim 1 which is 7-(L-phenylalanyl-L-arginyl)amino-4-methyl-coumarin.

22. The compound of claim 1 which is 7-(N$^\alpha$-carbobenzoxy-L-prolyl-L-phenylalanyl-L-arginyl)amino-4-methylcoumarin.

23. The compound of claim 1 which is 7-(L-propyl-L-phenylalanyl-L-arginyl)amino-4-methylcoumarin.

24. The compound of claim 1 which is 7-(N$^\alpha$-carbobenzoxy-L-propyl-L-arginyl)amino-4-methylcoumarin.

25. The compound of claim 1 which is 7-(N$^\alpha$-tert-butoxycarbonyl-L-valyl-L-prolyl-L-arginyl)amino-4-methylcoumarin.

* * * * *